(12) United States Patent
Lee et al.

(10) Patent No.: US 7,569,325 B2
(45) Date of Patent: Aug. 4, 2009

(54) MONOMER HAVING SULFONYL GROUP, POLYMER THEREOF AND PHOTORESIST COMPOSITION INCLUDING THE SAME

(75) Inventors: Jung-Youl Lee, Anyang-Si (KR);
Geun-Jong Yu, Jeonju-Si (KR);
Sang-Jung Kim, Incheon (KR);
Jae-Woo Lee, Bucheon-Si (KR);
Deog-Bae Kim, Seoul (KR); Jae-Hyun Kim, Seoul (KR)

(73) Assignee: Dongjin Semichem Co., Ltd., Incheon (KR)

( * ) Notice: Subject to any disclaimer, the term of this patent is extended or adjusted under 35 U.S.C. 154(b) by 0 days.

(21) Appl. No.: 11/923,392

(22) Filed: Oct. 24, 2007

(65) Prior Publication Data
US 2008/0102402 A1 May 1, 2008

(30) Foreign Application Priority Data
Oct. 25, 2006 (KR) .................... 10-2006-0103783

(51) Int. Cl.
G03F 7/004 (2006.01)
G03F 7/30 (2006.01)
C08F 226/00 (2006.01)
C07D 487/00 (2006.01)
C07C 303/28 (2006.01)

(52) U.S. Cl. .............. 430/270.1; 430/326; 430/330; 430/905; 430/910; 526/259; 526/280; 526/288; 540/476; 564/90

(58) Field of Classification Search ............ 430/270.1, 430/326, 330, 905, 910; 526/259, 280, 288; 540/476; 564/90
See application file for complete search history.

(56) References Cited

U.S. PATENT DOCUMENTS 6,114,083 A * 9/2000 Kawamura et al. ....... 430/270.1
6,153,352 A * 11/2000 Oohashi et al. ......... 430/270.1

FOREIGN PATENT DOCUMENTS

JP                  03211557       *  9/1991

* cited by examiner

*Primary Examiner*—John S Chu
(74) *Attorney, Agent, or Firm*—Birch, Stewart, Kolasch & Birch, LLP

(57) ABSTRACT

A photoresist monomer having a sulfonyl group, a polymer thereof and a photoresist composition containing the same are disclosed. The photoresist monomer is represented by following Formula.

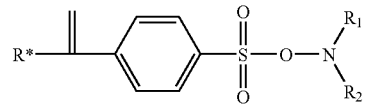

wherein, R* is a hydrogen atom or a methyl group, $R_1$ and $R_2$ are independently a $C_1$~$C_{20}$ alkyl group, a $C_4$~$C_{20}$ cycloalkyl group, a $C_6$~$C_{20}$ aryl group or a $C_7$~$C_{20}$ arylalkyl group, one of $R_1$ and $R_2$ may not exist, and $R_1$ and $R_2$ can be connected to form a ring.

6 Claims, No Drawings

MONOMER HAVING SULFONYL GROUP, POLYMER THEREOF AND PHOTORESIST COMPOSITION INCLUDING THE SAME

This application claims the priority benefit of Korean Patent Application No. 10-2006-0103783 filed on Oct. 25, 2006. All disclosure of the Korean Patent application is incorporated herein by reference.

FIELD OF THE INVENTION

This invention relates to a monomer, a polymer thereof and a photoresist composition including the same, and more specifically to a monomer having a sulfonyl group, a polymer thereof and a photoresist composition including the same.

BACKGROUNDS OF THE INVENTION

Recently, as the integration degree and the precision of semiconductor devices increase, the formation of ultra-fine photoresist patterns, which have a half pitch of less than 90 nm, is required in the photolithography process for producing the semiconductor devices. Thus, in the photolithography process, the wavelength of an exposure light is reduced to less than 193 nm, and various technologies for optimizing the pattern forming process have been being developed. In order to produce the fine photoresist patterns, it is also necessary to develop photosensitive materials having a low LER (Line Edge Roughness), a low PEB (Post Exposure Baking) temperature sensitivity, and a good dry etching resistance.

In order to improve the resolution and the process margin in forming the photoresist pattern, and to produce a more fine photoresist pattern, the photosensitive photoresist polymer should have a low activation energy in the deprotection reaction of a protecting group, in which the protecting group is adhered to the side chain of the photoresist polymer for inhibiting the dissolution of the polymer against a basic solution. Preferably, the photosensitive polymer should be materials having a low PEB(Post Exposure Baking) temperature sensitivity, that is, materials which are less affected by an acid. In summary, a fine photoresist pattern can be obtained by using a polymer which is less affected by an acid and whose main chain is decomposed by the light exposure.

SUMMARY OF THE INVENTION

Therefore, it is an object of the present invention to provide a monomer for photoresist, a polymer thereof and a photoresist composition including the same, which can improve the LER property and produce fine photoresist patterns with a light source of ultraviolet rays without a photo acid generator (PAG). It is another object of the present invention to provide a method for producing photoresist pattern by using the above-mentioned photoresist composition.

To accomplish these objects, the present invention provides a monomer for photoresist having a sulfonyl group represented by Formula 1.

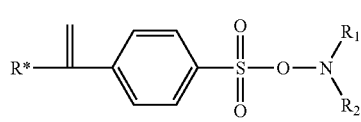

[Formula 1]

In Formula 1, R* is a hydrogen atom or a methyl group, $R_1$ and $R_2$ are independently a $C_1$~$C_{20}$ alkyl group, a $C_4$~$C_{20}$ cycloalkyl group, a $C_6$~$C_{20}$ aryl group or a $C_7$~$C_{20}$ arylalkyl group, one of $R_1$ and $R_2$ may not exist, and $R_1$ and $R_2$ can be connected to form a ring. If necessary, $R_1$ and $R_2$ may include a ketone group.

Also, the present invention provides a photoresist polymer which includes a repeating unit represented by following Formula 2 and can be decomposed by ultraviolet rays as well as an acid catalyst.

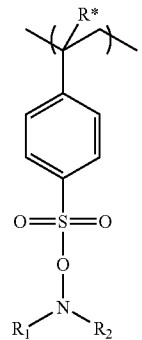

[Formula 2]

In Formula 2, R*, $R_1$ and $R_2$ are as defined in Formula 1.

DETAILED DESCRIPTION OF THE INVENTION

A more complete appreciation of the invention, and many of the attendant advantages thereof, will be better appreciated by reference to the following detailed description.

A monomer for photoresist having sulfonyl group according to the present invention is represented by following Formula 1.

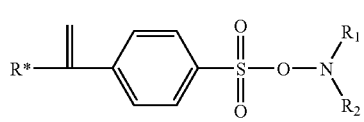

[Formula 1]

In Formula 1, R* is a hydrogen atom or a methyl group, $R_1$ and $R_2$ are independently a $C_1$~$C_{20}$ alkyl group, a $C_4$~$C_{20}$ cycloalkyl group, a $C_6$~$C_{20}$ aryl group or a $C_7$~$C_{20}$ arylalkyl group, one of $R_1$ and $R_2$ may not exist, and $R_1$ and $R_2$ can be connected to form a ring. When one of $R_1$ and $R_2$ is not exist, the existing functional group is connected to the nitrogen(N) by a double bond. If necessary, $R_1$ and $R_2$ may include a ketone group. Preferably, $R_1$ and $R_2$ are independently a $C_1$~$C_{10}$ alkyl group, a $C_6$~$C_{10}$ aryl group or a $C_7$~$C_{12}$ arylalkyl group. Examples of the photoresist monomer according to the present invention include

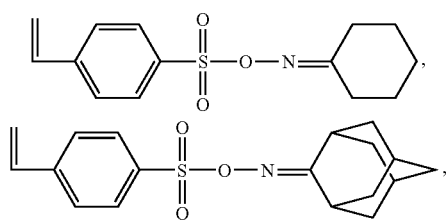

-continued

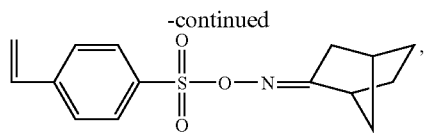

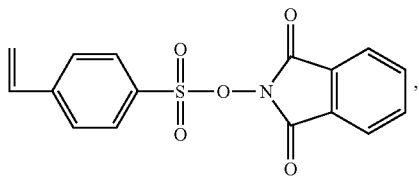

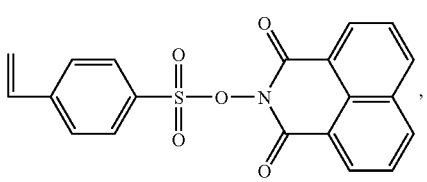

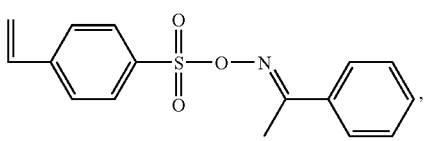

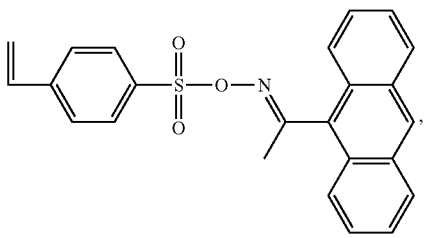

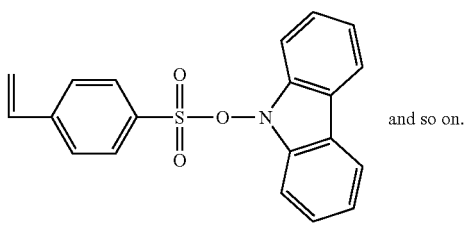

and so on.

In the photosensitive monomer of Formula 1 according to the present invention, the deprotection reaction can be carried out by an acid catalyst, but the deprotection reaction can also be carried out by ultraviolet rays without the acid catalyst, which is due to a photosensitive functional group, an oxime group(O—N) in the monomer. The deprotection reaction without using the acid catalyst also reduces the molecular weight of the polymer and changes the physical properties of the polymer. Thus, after a light exposure process, the compatibility of the polymer and a developer can be enhanced. Accordingly, in the developing process, fine photoresist patterns can be more easily produced and the line edge roughness property of the photoresist patterns can be improved in comparison with the conventional polymer.

The photoresist polymer having a sulfonyl group according to the present invention includes a repeating unit represented by following Formula 2.

[Formula 2]

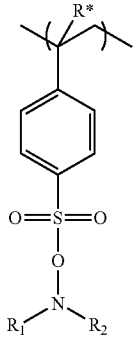

In Formula 2, $R^*$, $R_1$ and $R_2$ are as defined in Formula 1. In the photoresist polymer of the present invention, the amount of the repeating unit of Formula 2 is 20~60 mole %. The remaining repeating unit composing the photoresist polymer of the present invention can be one or more conventional repeating units, which can be conventionally used to produce a photoresist polymer. For example, the photoresist polymer according to the present invention can be represented by the following Formula 3.

[Formula 3]

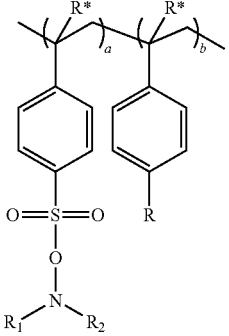

In Formula 3, $R^*$ is independently a hydrogen atom or a methyl group and $R_1$ and $R_2$ are as defined in Formula 2. R is a hydrogen atom, a $C_1$~$C_{10}$ alkyl group, a $C_6$~$C_{10}$ aryl group or a $C_7$~$C_{12}$ arylalkyl group. a and b independently represent mole % of repeating units constituting the polymer, and are 1~99 mole % and 1~99 mole %, respectively. Preferably, a:b is 20~60 mole %: 40~80 mole %. If necessary, R may include a hydroxyl group or an ester group.

Specific examples of Formula 2 can be represented by following Formula 4.

[Formula 4]

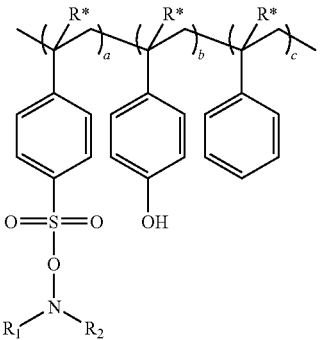

In Formula 4, R* is independently a hydrogen atom or a methyl group. $R_1$ and $R_2$ are as defined in Formula 2. a, b and c independently represent mole % of repeating units constituting the polymer, and are 1~98 mole %, 1~98 mole % and 1~98 mole %, respectively. Preferably, a:b:c is 1~60 mole %:1~60 mole %:1~50 mole %.

The photosensitive polymer of the present invention may further include other auxiliary monomers, such as cycloolefin monomer (for example, maleic anhydride), another conventional monomer for forming a photosensitive polymer, a cross-linking monomer, and so on. The preferable amount of the auxiliary monomers is 0~5 mole % with respect to the total repeating unit. The photosensitive polymer according to the present invention may be a block copolymer or a random copolymer. The weight-average molecular weight (Mw) of the photosensitive polymer is preferably 3,000 to 20,000 and more preferably 3,000 to 15,000. The polydispersity thereof is preferably 1.0 to 5.0 and more preferably 1.0 to 2=2. If the weight-average molecular weight and the polydispersity of the photosensitive polymer deviate from the above mentioned ranges, the physical property of the photoresist layer can be deteriorated, the formation of photoresist layer may be difficult and the contrast of the photoresist patterns can be deteriorated.

The photoresist monomer of the present invention can be prepared by, for example, a) reacting an oxime compound and a sulfonyl chloride compound at the temperature of 0° C. or less, as shown in Reaction 1, b) washing the reaction product with water for several times to remove an organic base, and c) recrystallizing the reaction product with hexane.

[Reaction 1]

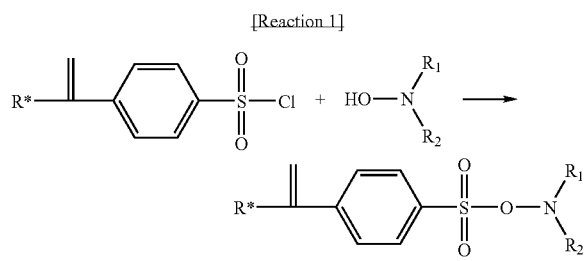

The photosensitive polymer of the present invention can be prepared by a conventional polymerization reaction using the monomer of Formula 1 and other conventional monomer(s). In the polymerization, a conventional polymerization initiator can be widely used, and the exemplary initiator includes, but is not limited to, azobis(isobutyronitrile) (AIBN).

The photoresist composition according to the present invention can be prepared by mixing the photosensitive polymer containing the monomer represented by Formula 1, a photo-acid generator for generating an acid, and an organic solvent, and, if necessary, various additives. The preferable concentration of the solid components in the photoresist composition is 1~30 weight % with respect to the total photoresist composition. The photoresist composition can be used after filtering with 0.2 μm filter.

As the photo-acid generator, any conventional photo-acid generator, which can generate an acid when exposed to light, can be used. The non-limiting examples of the photo-acid generator include an organic sulfonic acid, an onium salt or the mixtures thereof. The preferable amount of the photo-acid generator is 0.1 to 20 weight parts with respect to 100 weight parts of the photoresist polymer. If the amount of the photo-acid generator is less than 0.1 weight parts, the light sensitivity of the photoresist composition may decrease. If the amount of the photo-acid generator is more than 20 weight parts, the profile of the resist patterns may be deteriorated because the photo-acid generator absorbs a lot of ultraviolet rays and a large quantity of acid is excessively produced from the photo-acid generator.

As the organic solvent of the photoresist composition of the present invention, various conventional organic solvents for a photoresist composition can be used. Exemplary organic solvent include, but are not limited to, ethyleneglycol monomethylethyl, ethyleneglycol monoethylether, ethyleneglycol monomethylether, diethyleneglycol monoethylether, propyleneglycol monomethyletheracetate(PGMEA), toluene, xylene, methylethylketone, cyclohexanone, ethyl 2-hydroxy propionate, ethyl 2-hydroxy-2-methyl propionate, ethoxyethyl acetate, hydroxyethyl acetate, methyl 2-hydroxy-3-methylbutanoate, methyl 3-methoxy-2-methylpropionate, ethyl 3-ethoxy propionate, ethyl 3-methoxy-2-methyl propionate, ethyl acetate, butyl acetate, and the mixtures thereof. The preferable amount of the organic solvent is 300~5000 weight parts with respect to the total photoresist polymer 100 weight parts.

In addition, the photoresist composition of the present invention may further include an organic base. The preferable amount of the organic base is 0.01~10 weight %. Exemplary organic base includes, but not limited to, triethylamine, triisobutylamine, triisooctylamine, diethanolamine, triethanolamine and the mixtures thereof.

In order to form a photoresist pattern with the photoresist composition according to the present invention, the following conventional photolithography process can be carried out. First, the photoresist composition is applied or coated on a substrate such as silicon wafer, an aluminum substrate, and so on, for example, with a spin coater to form a photoresist layer. The photoresist layer is exposed to a light of a predetermined pattern. After the exposure, if necessary, the photoresist pattern is thermally treated(heated), which is called as PEB (Post Exposure Bake), and is developed to form the photoresist pattern. As the developing solution for the developing process, an alkali aqueous solution including an alkali compound such as sodium hydroxide, potassium hydroxide, sodium carbonate, tetramethylammonium hydroxide (TMAH) of the concentration of 0.1 to 10 weight % can be used. If necessary, the developing solution may further include water-soluble organic solvent such as methanol or ethanol and a surfactant of a proper amount. After developing, a cleaning process of the substrate can be carried out, in which the substrate is washed with purified water.

Hereinafter, the preferable examples are provided for better understanding of the present invention. However, the present invention is not limited to the following examples.

EXAMPLE 1-1

Preparation of Monomer Represented by Following Formula 2a 12.4 g (0.11 mol) of the compound represented by Formula 1a was dissolved in 100 mL of tetrahydrofuran (THF) (solvent) and then 15.0 g of triethylamine (organic base) was added to the reaction solution. The solution was stirred with maintaining the temperature of the reaction solution at 0° C. 20.2 g (0.1 mol) of 4-chlorosulfonyl styrene which was dissolved in 10 mL of THF was slowly added into the reaction solution and the reaction solution was stirred for 12 hours at room temperature. After completion of the reaction, 100 mL of cold distilled water was poured to the reaction solution and the reaction solution was extracted by using 200 mL of diethyl ether for 3 times. The extracted solution was dried with anhydrous magnesium sulfate and was distilled under the reduced pressure. The compound obtained by the distillation was recrystallized with hexane to obtain a monomer represented by Formula 2a (Yield: 91%). $^1$H-NMR (CDCl$_3$, internal standard): δ (ppm) 7.88 (CH, 2H), 7.50 (CH, 2H), 6.63 (CH, 1H), 5.63 (CH$_2$, 1H), 5.18 (CH$_2$, 1H), 1.59 (CH$_2$, 4H), 1.26 (CH$_2$, 4H), 1.19 (CH$_2$, 2H)

[Formula 1a]

[Formula 2a]

EXAMPLE 1-2

Preparation of Monomer Represented by Following Formula 2b

Except for using 18.2 g (0.11 mol) of the compound represented by Formula 1b instead of 12.4 g of the compound represented by Formula 1a, the reaction was carried out in the same manner as described in Example 1-1 to obtain a monomer of following Formula 2b (Yield: 85%). $^1$H-NMR (CDCl$_3$, internal standard): δ (ppm) 7.85 (CH, 2H), 7.47 (CH, 2H), 6.59 (CH, 1H), 5.60 (CH$_2$, 1H), 5.16 (CH$_2$, 1H), 1.74 (CH$_2$, 4H), 1.44 (CH$_2$, 6H). 1.21 (CH, 2H), 1.08 (CH$_2$, 2H)

[Formula 1b]

[Formula 2b]

EXAMPLE 1-3

Preparation of Monomer Represented by Formula 2c

Except for using 13.8 g (0.11 mol) of the compound represented by Formula 1c instead of 12.4 g of the compound represented by Formula 1a, the reaction was carried out in the same manner as described in Example 1-1 to obtain a monomer of following Formula 2c (Yield: 87%). $^1$H-NMR (CDCl$_3$, internal standard): δ (ppm) 7.86 (CH, 2H), 7.47 (CH, 2H), 6.60 (CH, 1H), 5.61 (CH$_2$, 1H), 5.15 (CH$_2$, 1H), 1.69 (CH$_2$, 2H), 1.60 (CH$_2$, 1H), 1.52 (CH$_2$, 1H). 1.46 (CH$_2$, 2H), 1.41 (CH$_2$, 2H), 1.24 (CH$_2$, 2H)

[Formula 1c]

[Formula 2c]

EXAMPLE 1-4

Preparation of Monomer Represented by Formula 2d

Except for using 17.9 g (0.11 mol) of the compound represented by Formula 1d instead of 12.4 g of the compound represented by Formula 1a, the reaction was carried out in the same manner as described in Example 1-1 to obtain a monomer of following Formula 2d (Yield: 94%). $^1$H-NMR (CDCl$_3$, internal standard): δ (ppm) 8.15 (CH, 2H), 7.86 (CH, 2H), 7.60 (CH, 2H), 7.49 (CH, 2H), 6.61 (CH, 1H), 5.61 (CH$_2$, 1H), 5.15 (CH$_2$, 1H)

[Formula 1d]

[Formula 2d]

EXAMPLE 1-5

Preparation of Monomer Represented by Formula 2e

Except for using 23.4 g (0.11 mol) of the compound represented by Formula 1e instead of 12.4 g of the compound represented by Formula 1a, the reaction was carried out in the same manner as described in Example 1-1 to obtain a monomer of following Formula 2e (Yield: 83%). $^1$H-NMR (CDCl$_3$, internal standard): δ (ppm) 8.02 (CH, 2H), 7.98 (CH, 2H), 7.86 (CH, 2H), 7.71 (CH, 2H), 7.49 (CH, 2H), 6.61 (CH, 1H), 5.61 (CH$_2$, 1H), 5.15 (CH$_2$, 1H)

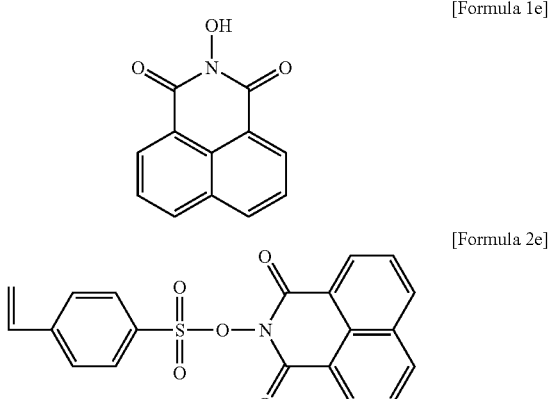

[Formula 1e]

[Formula 2e]

EXAMPLE 1-6

Preparation of Monomer Represented by Formula 2f

Except for using 14.9 g (0.11 mol) of the compound represented by Formula 1f instead of 12.4 g of the compound represented by Formula 1a, the reaction was carried out in the same manner as described in Example 1-1 to obtain a monomer of following Formula 2f (Yield: 92%). $^1$H-NMR (CDCl$_3$, internal standard): δ (ppm) 7.87 (CH, 2H), 7.66 (CH, 2H), 7.51 (CH, 2H), 7.37 (CH, 3H), 6.59 (CH, 1H), 5.62 (CH$_2$, 1H), 5.19 (CH$_2$, 1H), 1.89 (CH$_3$, 3H)

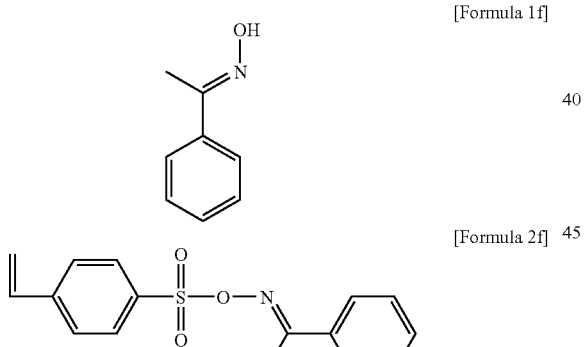

[Formula 1f]

[Formula 2f]

EXAMPLE 1-7

Preparation of Monomer Represented by Formula 2g

Except for using 25.8 g (0.11 mol) of the compound represented by Formula 1g instead of 12.4 g of the compound represented by Formula 1a, the reaction was carried out in the same manner as described in Example 1-1 to obtain a monomer of following Formula 2g (Yield: 81%). $^1$H-NMR (CDCl$_3$, internal standard): δ (ppm) 8.45 (CH, 2H), 7.95 (CH, 4H), 7.87 (CH, 2H), 7.65 (CH, 2H), 7.49 (CH, 2H), 7.32 (CH, 1H), 6.62 (CH, 1H), 5.61 (CH$_2$, 1H), 5.19 (CH$_2$, 1H), 1.94 (CH$_3$, 1H)

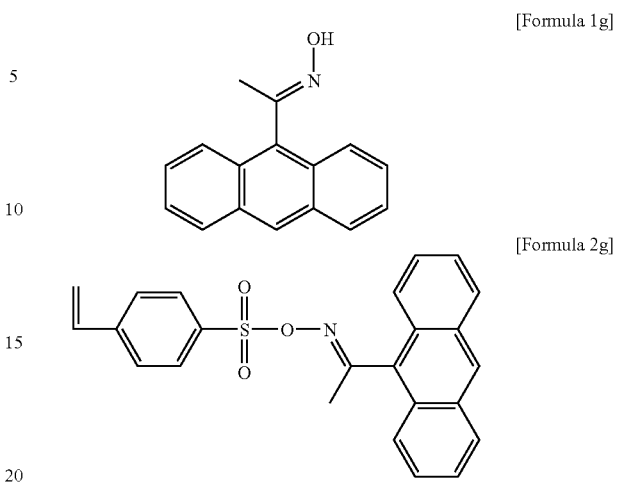

[Formula 1g]

[Formula 2g]

EXAMPLE 1-8

Preparation of Monomer Represented by Formula 2h

Except for using 20.1 g (0.11 mol) of the compound represented by Formula 1h instead of 12.4 g of the compound represented by Formula 1a, the reaction was carried out in the same manner as described in Example 1-1 to obtain a monomer of following Formula 2h (Yield: 89%). $^1$H-NMR (CDCl$_3$, internal standard): δ (ppm) 7.89 (CH, 2H), 7.69 (CH, 4H), 7.50 (CH, 2H), 7.42 (CH, 4H), 6.59 (CH, 1H), 5.64 (CH$_2$, 1H), 5.20 (CH$_2$, 1H)

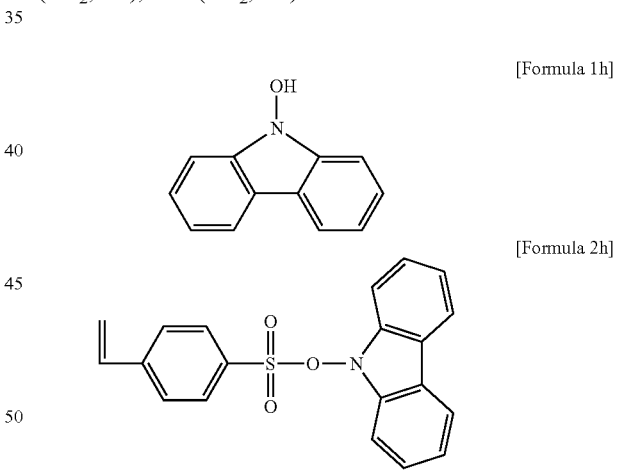

[Formula 1h]

[Formula 2h]

EXAMPLE 2-1

Preparation of Polymer Represented by Formula 3a 300 mL of tetrahydrofuran (THF) was added to a 500 mL 4-neck flask on which a Liebig condenser, a temperature controller and a nitrogen injector were mounted, then nitrogen gas was injected and the reaction solution was stirred for 30 minutes. 41.86 g of the monomer of Formula 2a, 48.62 g of 4-acetoxystyrene, 5.21 g of styrene and 2.73 of azobis(isobutyronitrile) (AIBN) were added to the reaction solution and the mixture was stirred for 30 minutes under nitrogen atmosphere at 40° C. Thereafter, the reaction solution was heated to 70° C. and the polymerization was performed for 24 hours. After the completion of the polymerization, the reaction solution was cooled to room temperature and the reaction solution was added into 3 L of hexane to obtain a precipitate. Next, the obtained precipitate was filtered, washed with 2 L of hexane for several times and vacuum-dried. 300 mL of methanol and 50 mL of 30% $NH_4OH$ aqueous solution were added to the flask containing the dried polymer, and the mixture was slowly stirred at 50° C. to completely dissolve the polymer and further stirred for 30 minutes. The dissolved solution was added into 1.5 L of water to obtain a precipitate. The obtained precipitate was filtered, washed with 2 L of purified water for several times, and vacuum-dried for 2 days to prepare 67.92 g of a photosensitive polymer of following Formula 3a (Yield: 75%, mol % of the repeating units, a:b:c=30 mol %:60 mole %:10 mol %). The molecular weight (Mw) and polydispersity (PD) of the prepared polymer were measured with GPC (Gel permeation chromatography), and Mw was 18,600 and PD was 1.94.

[Formula 3a]

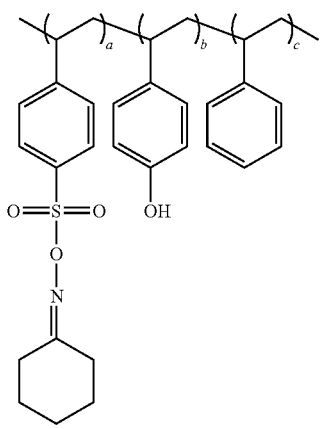

EXAMPLE 2-2

Preparation of Polymer Represented by Formula 3b

Except for using 49.67 g of the monomer of Formula 2b instead of 41.86 g of the monomer of Formula 2a, the polymerization reaction was carried out in the same manner as described in Example 2-1 to obtain a polymer of following Formula 3b (Yield: 71%, mol % of the repeating unit, a:b:c=30 mol %:60 mole %:10 mol %). From the GPC analysis of the polymer, Mw was 17,100 and PD was 1.89.

[Formula 3b]

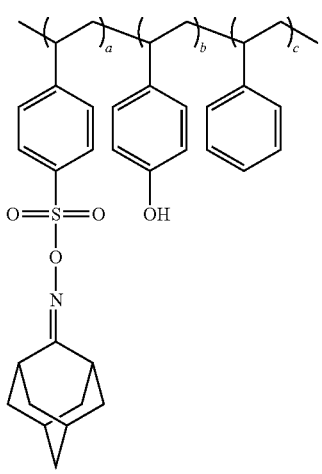

EXAMPLE 2-3

Preparation of Polymer Represented by Formula 3c

Except for using 43.66 g of the monomer of Formula 2c instead of 41.86 g of the monomer of Formula 2a, the polymerization reaction was carried out in the same manner as described in Example 2-1 to obtain a polymer of following Formula 3c (Yield: 74%, mol % of the repeating unit, a:b:c=30 mol %:60 mole %:10 mol %). From the GPC analysis of the polymer, Mw was 19,500 and PD was 1.92.

[Formula 3c]

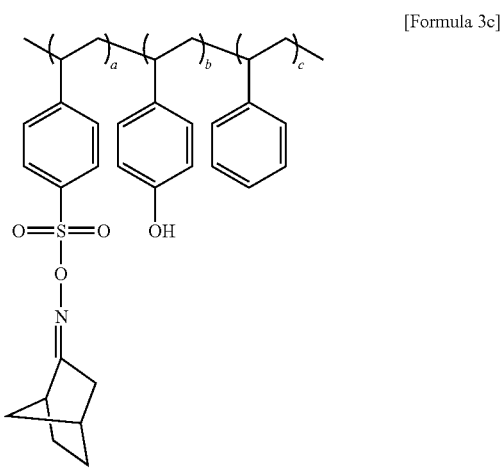

EXAMPLE 2-4

Preparation of Polymer Represented by Formula 3d

Except for using 49.36 g of the monomer of Formula 2d instead of 41.86 g of the monomer of Formula 2a, the polymerization reaction was carried out in the same manner as described in Example 2-1 to obtain a polymer of following Formula 3d (Yield: 69%, mol % of the repeating unit, a:b:c=30 mol %: 60 mole %:10 mol %). From the GPC analysis of the polymer, Mw was 18,200 and PD was 2.01.

[Formula 3d]

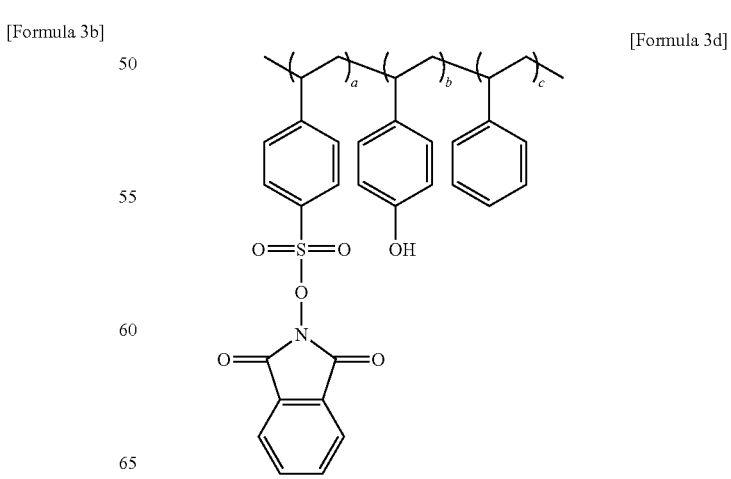

EXAMPLE 2-5

Preparation of Polymer Represented by Formula 3e

Except for using 56.86 g of the monomer of Formula 2e instead of 41.86 g of the monomer of Formula 2a, the polymerization reaction was carried out in the same manner as described in Example 2-1 to obtain a polymer of following Formula 3e (Yield; 78%, mol % of the repeating unit, a:b:c=30 mol %:60 mole %:10 mol %). From the GPC analysis of the polymer, Mw was 16,900 and PD was 2.04.

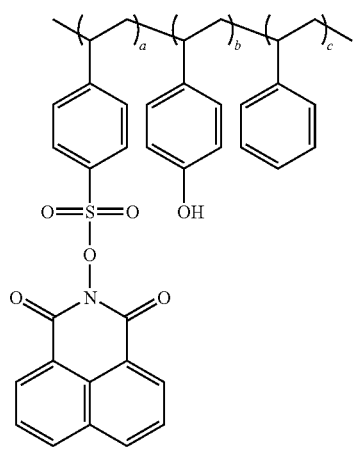

[Formula 3e]

EXAMPLE 2-6

Preparation of Polymer Represented by Formula 3f

Except for using 45.16 g of the monomer of Formula 2f instead of 41.86 g of the monomer of Formula 2a, the polymerization reaction was carried out in the same manner as described in Example 2-1 to obtain a polymer of following Formula 3f (Yield; 72%, mol % of the repeating unit, a:b:c=30 mol %:60 mole %:10 mol %). From the GPC analysis of the polymer, Mw was 18,200 and PD was 1.98.

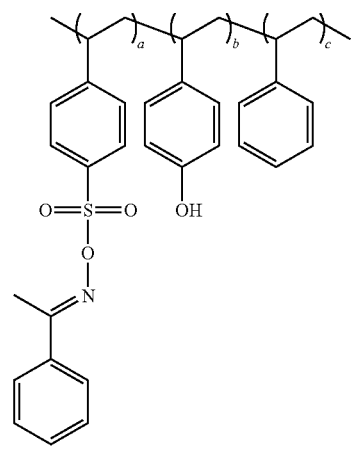

[Formula 3f]

EXAMPLE 2-7

Preparation of Polymer Represented by Formula 3g

Except for using 60.17 g of the monomer of Formula 2g instead of 41.86 g of the monomer of Formula 2a, the polymerization reaction was carried out in the same manner as described in Example 2-1 to obtain a polymer of following Formula 3g (Yield: 68%, mol % of the repeating unit, a:b:c=30 mol %:60 mole %:10 mol %). From the GPC analysis of the polymer, Mw was 16,900 and PD was 1.85.

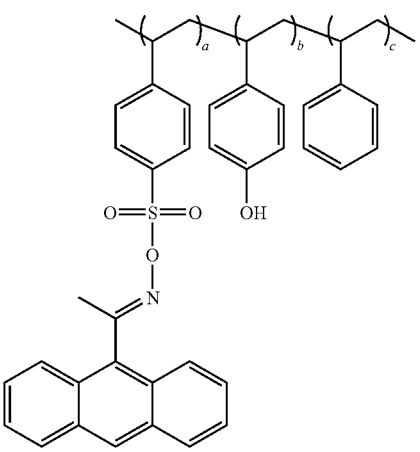

[Formula 3g]

EXAMPLE 2-8

Preparation of Polymer Represented by Formula 3h

Except for using 52.36 g of the monomer of Formula 2h instead of 41.86 g of the monomer of Formula 2a, the polymerization reaction was carried out in the same manner as described in Example 2-1 to obtain a polymer of following Formula 3h (Yield: 75%, mol % of the repeating unit, a:b:c=30 mol %:60 mole %:10 mol %). From the GPC analysis of the polymer, Mw was 17,400 and PD was 1.91.

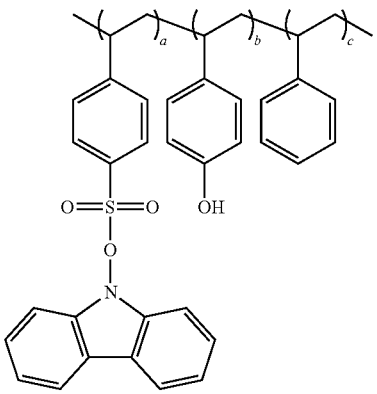

[Formula 3h]

EXAMPLES 3-1 THROUGH 3-8

Preparation of Photoresist Composition 1.8 g of the photoresist polymer (Formula 3a to 3h) prepared in Examples 2-1 to 2-8, 0.08 g of triphenylsulfonium triflate and 0.03 g of triethanolamine were dissolved in 30 g of propyleneglycol monomethylether acetate (PGMEA). Then the dissolved mixtures were filtered with a 0.20 μm filter to prepare photoresist compositions.

COMPARATIVE EXAMPLE 1

Preparation of Photoresist Composition

Except for using 4.08 g of 4-acetoxystyrene and 3.58 g of t-butyl methacrylate without using the monomer of Formula 2a, the polymerization reaction was carried out in the same manner as described in Example 2-1 to produce a polymer of Formula 5. In the polymer of Formula 5, the amounts (mole %) of the two repeating units are 50 mole % and 50 mole %, respectively. From the GPC analysis of the polymer, Mw was 14,700 and PD was 2.22.

Next, 1.8 g of the photosensitive polymer of Formula 5, 0.08 g of triphenylsulfonium triflate and 0.03 g of triethanolamine were dissolved in 30 g of propyleneglycol monomethyletheracetate (PGMEA), and filtered with a 0.20 μm filter to prepare the a photoresist composition.

[Formula 5]

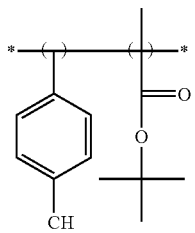

EXAMPLE 4

Formation of Photoresist Pattern Using the Photoresist Composition

The photoresist composition prepared in Examples 3-1~3-8 and Comparative example 1 was spin-coated to a thickness of 0.1 μm on a silicon wafer, which was treated with hexamethyldisilazane(HMDS), to form a photoresist thin-layer. The photoresist layer was pre-baked at the temperature of 130° C. for 90 seconds in an oven or on a hot plate, and was optimum exposed with a KrF excimer laser having 0.5 of an aperture number. Next the photoresist layer was post-baked at the temperature of 130° C. for 90 seconds. Thereafter, the baked wafer was developed with 2.38 weight % of tetramethylammonium hydroxide(TMAH) solution for about 30 seconds, thereby forming a 0.20 μm line/space patterns. The line width variations of the produced photoresist patterns are set forth in Table 1.

TABLE 1

| Photoresist composition | Resolution (nm) | Line width variation (nm) |
|---|---|---|
| Example 3-1 (Formula 3a) | 200 | 3.2 |
| Example 3-2 (Formula 3b) | 200 | 3.5 |
| Example 3-3 (Formula 3c) | 200 | 3.1 |
| Example 3-4 (Formula 3d) | 200 | 3.4 |
| Example 3-5 (Formula 3e) | 200 | 3.3 |
| Example 3-6 (Formula 3f) | 200 | 3.2 |
| Example 3-7 (Formula 3g) | 200 | 3.4 |
| Example 3-8 (Formula 3h) | 200 | 3.8 |
| Comparative Example 1 (Formula 5) | 200 | 4.5 |

As shown Table 1, the photoresist composition containing photosensitive polymer (Formula 3a-3h) of the present invention has superior line width stability compared to the photoresist composition containing the conventional chemically amplified photosensitive polymer (Formula 5). In addition, the photoresist layers, which were prepared with the photoresist composition of Examples 3-1~3-8, were exposed with EUV exposure apparatus, which results in successful formations of 50 nm line/space patterns.

As described above, in a lithography process, the polymer according to the present invention can be decomposed by ultraviolet rays without PAG, so a fine pattern can be formed. In addition, the polymer according to the present invention is decomposed by ultraviolet rays as well as an acid in case that the composition including the polymer also contains the PAG. So, the energy sensitivity of the polymer increases. In addition, the photoresist polymer and the photoresist composition containing the same of the present invention can improve the line edge roughness of the photoresist pattern since the decomposed sulfonic acid is connected to the polymer, and the diffusion of the acid is restricted.

The invention claimed is:

1. A photoresist monomer including sulfonyl group represented by following Formula 1,

[Formula 1]

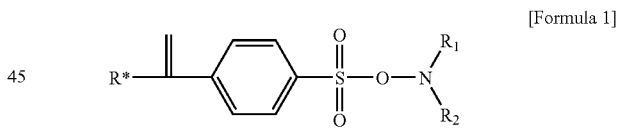

wherein, R* is a hydrogen atom or a methyl group, $R_1$ and $R_2$ are independently a $C_1$~$C_{20}$ alkyl group, a $C_4$~$C_{20}$ cycloalkyl group, a $C_6$~$C_{20}$ aryl group or a $C_7$~$C_{20}$ arylalkyl group, and one of $R_1$ and $R_2$ may not exist or $R_1$ and $R_2$ can be connected to form the following monomer

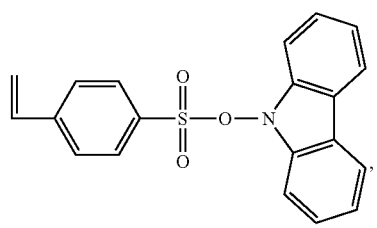

provided that when one of $R_1$ and $R_2$ is absent, the monomer is selected from the group consisting of

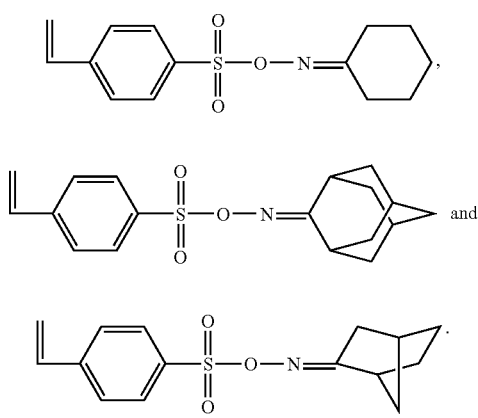

2. A photoresist polymer containing a repeating unit represented by following Formula 2,

[Formula 2]

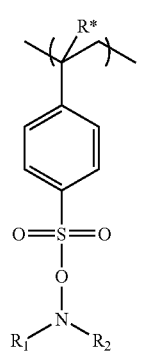

wherein, R* is a hydrogen atom or a methyl group, $R_1$ and $R_2$ are independently a $C_1$~$C_{20}$ alkyl group, a $C_4$~$C_{20}$ cycloalkyl group, a $C_6$~$C_{20}$ aryl group or a $C_7$~$C_{20}$ arylalkyl group, group, and one of $R_1$ and $R_2$ may not exist, and $R_1$ and $R_2$ can be connected to form the following repeating unit

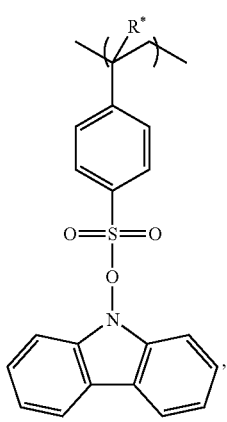

provided that when one of $R_1$ and $R_2$ is absent, the repeating unit is selected from the group consisting of

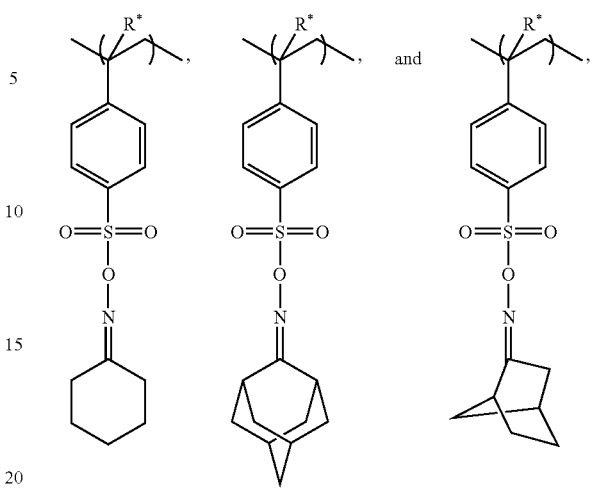

3. The photoresist polymer of claim 2, wherein the photoresist polymer is represented by following Formula 3,

[Formula 3]

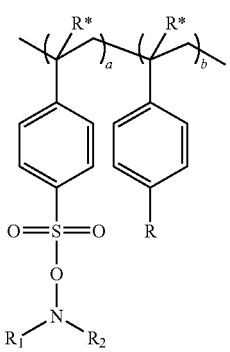

wherein, R* is independently a hydrogen atom or a methyl group; $R_1$ and $R_2$ are independently a $C_1$~$C_{20}$ alkyl group, a $C_4$~$C_{20}$ cycloalkyl group, a $C_6$~$C_{20}$ aryl group or a $C_7$~$C_{20}$ arylalkyl group, one of $R_1$ and $R_2$ may not exist, R is a hydrogen atom, a $C_1$~$C_{10}$ alkyl group, a $C_6$~$C_{10}$ aryl group or a $C_7$~$C_{12}$ arylalkyl group; and a and b independently represent mole % of repeating units constituting the polymer, and are 1~99 mole % and 1~99 mole %, respectively.

4. The photoresist polymer of claim 2, wherein the photoresist polymer is represented by following Formula 4,

[Formula 4]

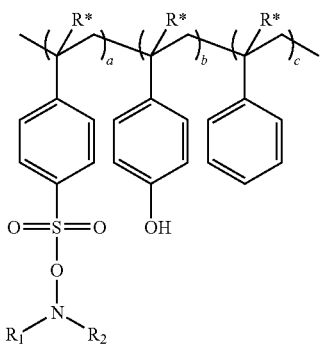

wherein, R* is independently a hydrogen atom or a methyl group; $R_1$ and $R_2$ are independently a $C_1$~$C_{20}$ alkyl group, a $C_4$~$C_{20}$ cycloalkyl group, a $C_6$~$C_{20}$ aryl group or a $C_7$~$C_{20}$ arylalkyl group, one of $R_1$ and $R_2$ may not exist, R is a hydrogen atom, a $C_1$~$C_{10}$ alkyl group, a $C_6$~$C_{10}$ aryl group or a $C_7$~$C_{12}$ arylalkyl group; and a, b and c independently represent mole % of repeating units constituting the polymer, and are 1~98 mole %, 1~98 mole % and 1~98 mole %, respectively.

5. A photoresist composition comprising:

a photoresist polymer containing monomer represented by Formula 1,

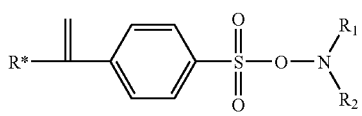

[Formula 1]

wherein, R* is a hydrogen atom or a methyl group, $R_1$ and $R_2$ are independently a $C_1$~$C_{20}$ alkyl group, a $C_4$~$C_{20}$ cycloalkyl group, a $C_6$~$C_{20}$ aryl group or a $C_7$~$C_{20}$ arylalkyl group, and one of $R_1$ and $R_2$ may not exist;

a photo acid generator for generating acid; and an organic solvent;

wherein the amount of the photo acid generator is 0.1 to 20 weight parts with respect to 100 weight parts of the photoresist polymer and the amount of the organic solvent is 300 to 5000 weight parts with respect to 100 weight parts of the photoresist polymer.

6. A method for forming a photoresist pattern, comprising the steps of:

a) coating a photoresist composition on a substrate to form a photoresist layer;

b) exposing the photoresist layer to a light;

c) heating the exposed photoresist layer; and d) developing the heated photoresist layer to form the photoresist pattern, wherein the photoresist composition comprises a photoresist polymer containing monomer represented by the Formula 1, a photo-acid generator for generating an acid and an organic solvent,

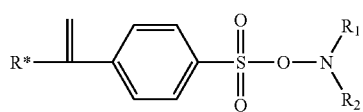

[Formula 1]

wherein, R* is a hydrogen atom or a methyl group, $R_1$ and $R_2$ are independently a $C_1$~$C_{20}$ alkyl group, a $C_4$~$C_{20}$ cycloalkyl group, a $C_6$~$C_{20}$ aryl group or a $C_7$~$C_{20}$ arylalkyl group, and one of $R_1$ and $R_2$ may not exist.

* * * * *